United States Patent
Frank et al.

(10) Patent No.: US 7,713,418 B2
(45) Date of Patent: May 11, 2010

(54) PROCESS FOR RECOVERING ORGANIC COMPOUNDS FROM AQUEOUS STREAMS CONTAINING SAME

(75) Inventors: Timothy C. Frank, Midland, MI (US);
Thomas C. Thyne, Midland, MI (US);
Felipe A. Donate, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 598 days.

(21) Appl. No.: 10/590,685

(22) PCT Filed: Feb. 18, 2005

(86) PCT No.: PCT/US2005/005308

§ 371 (c)(1),
(2), (4) Date: Aug. 25, 2006

(87) PCT Pub. No.: WO2005/087692

PCT Pub. Date: Sep. 22, 2005

(65) Prior Publication Data

US 2007/0193960 A1    Aug. 23, 2007

Related U.S. Application Data

(60) Provisional application No. 60/548,404, filed on Feb. 27, 2004.

(51) Int. Cl.
*B01D 15/00* (2006.01)
*C02F 1/44* (2006.01)
*B01D 11/04* (2006.01)

(52) U.S. Cl. ..................... 210/639; 210/634

(58) Field of Classification Search ............... 210/634, 210/639
See application file for complete search history.

(56) References Cited

U.S. PATENT DOCUMENTS 3,556,739 A    1/1971    Baniel et al.

(Continued)

OTHER PUBLICATIONS

Allen et al. Use of glycol ethers for selective release of periplasmic proteins from gram-negative bacteria. Biotechnol. Prog. (2007) vol. 23, 1163-1170.*

(Continued)

*Primary Examiner*—Krishnan S Menon
*Assistant Examiner*—Katherine Zalasky
(74) *Attorney, Agent, or Firm*—Dragan J. Karadzic; Paul D. Hayhurst

(57) ABSTRACT

A method for a liquid-liquid extraction of hydrophilic organic compounds from aqueous solutions thereof is described. The method generally includes intermixing a sufficient quantity of a specified glycol ether with the aqueous liquor at a first temperature to form a suspension comprising an aqueous raffinate phase and a glycol ether extract phase; separating the glycol ether extract phase from the aqueous raffinate phase; heating the glycol ether extract phase to a second, higher temperature to form a suspension comprising an aqueous extract phase containing a portion of the hydrophilic organic compound and a glycol ether raffinate phase; and separating this glycol ether raffinate phase from the aqueous extract phase. The selected glycol ether has an inverse solubility in water and the partition ratio, value K, for the hydrophilic organic compound is greater than 0.1. This method is useful for recovering valuable hydrophilic organic acids produced via fermentation or produced or used in various manufacturing processes.

13 Claims, 1 Drawing Sheet

U.S. PATENT DOCUMENTS

| | | |
|---|---|---|
| 4,322,550 A | 3/1982 | Kimble |
| 4,954,260 A * | 9/1990 | Ludmer et al. .............. 210/634 |
| 5,426,219 A | 6/1995 | Lehnhardt et al. |
| 5,628,906 A | 5/1997 | Shinnar et al. |
| 6,229,046 B1 | 5/2001 | Eyal et al. |
| 6,320,077 B1 | 11/2001 | Eyal et al. |
| 2008/0021204 A1 | 1/2008 | Donate et al. |
| 2009/0023902 A1 | 1/2009 | Frank et al. |

OTHER PUBLICATIONS

Robins, L.A. and R. W. Cusack, "Liquid-Liquid Extraction Operations and Equipment", Perry's Chemical Engineers' Handbook, 1997, Section 15, $7^{th}$ Edition, R.H. Perry and D.W. Green, editors, McGraw-Hill, New York.

Christensen, Scott P., et al., "Mutual Solubility and Lower Critical Solution Temperature for Water + Glycol Ether Systems", J. Chem. Eng. Data 2005, 50, 869-877.

* cited by examiner

PROCESS FOR RECOVERING ORGANIC COMPOUNDS FROM AQUEOUS STREAMS CONTAINING SAME

CROSS-REFERENCE TO RELATED APPLICATIONS

This application is filed under 35 USC §371 in the United States and is based on PCT Application PCT/US2005/005308, filed Feb. 18, 2005, now pending, which claims the benefit of U.S. Provisional Patent Application Ser. No. 60/548,404, filed Feb. 27, 2004.

BACKGROUND OF THE INVENTION

The present invention relates to a process for recovering hydrophilic organic compounds from aqueous streams containing same by liquid-liquid extraction.

Many valuable hydrophilic organic compounds such as carboxylic acids, sulfonic acids, polyhydroxy compounds, amino acids and amides are produced or utilized within manufacturing processes involving aqueous streams. Examples include production of carboxylic acids via fermentation processes and utilization of sulfonic acids as catalysts for esterification reactions. Various methods, such as, for example, steam stripping, liquid-liquid extraction, liquid-solid adsorption, chromatography and membrane-based methods, are known for recovery of these valuable hydrophilic compounds from aqueous liquor containing same such as, for example, fermentation broths and waste water streams.

For example, U.S. Pat. No. 5,426,219 (W. Lenhardt et al.) discloses a process for recovering an organic acid such as lactic acid from an aqueous solution thereof. The process involves extracting the aqueous solution containing an organic acid with a mixture consisting of water, a mineral acid in quantity effective to maintain pH of the mixture between 1.0 and 4.5, and an oxygenated solvent which has limited solubility with water and the aqueous solution to produce a solvent extract and a first raffinate. The oxygenated solvent has from 6-8 carbon atoms and at least one hydroxyl, ester, ketone, ether, carbonyl or amid group. The solvent extract is then back extracted with an aqueous liquid to produce an organic acid-rich aqueous extract and an organic acid-depleted solvent raffinate.

U.S. Pat. No. 3,556,739 (A. Baniel et al.) discloses a process for extracting a technical-grade phosphoric acid with certain organic solvents selected from the group of ethers, ketones and glycol ethers having from 2 to 15 carbon atoms. These solvents (a) practically do not extract phosphoric acid from an aqueous solution thereof having concentration of phosphoric acid below 35 percent by weight, and (b) extract a substantial portion of phosphoric acid from an aqueous solution thereof having a concentration of phosphoric acid greater than 35 percent by weight.

U.S. Pat. No. 4,322,550 (J. Kimble) discloses a process for recovery of mercaptoalkanoic acids from an aqueous solution thereof by a liquid-liquid extraction operation using at least one alkanoic acid ester and an alkylene glycol ether.

U.S. Pat. No. 5,628,906 (R. Shinnar et al.) discloses a liquid-liquid extraction process wherein a solution of a solute in a native solvent, for example water, is mixed with a primary solvent, which is soluble with the native solvent, and subsequently adding a modifier, which is insoluble with either the native or the primary solvent. By adding the modifier, the solubility of the primary solvent with the native solvent is changed, thereby causing a near instantaneous phase separation. The solute is concentrated in the primary-solvent-rich phase. Examples of some primary solvents are acetaldehyde, acetic acid, acetonitrile, butanoic acid, ethanol, formic acid, methanol, propanoic acid, 1-propanol, 2-propanol, 2-propanone, propenoic acid, pyridine and triethylene glycol dimethyl ether. Examples of some modifiers are 3-methylbutyl ester of acetic acid, benzene, cyclohexane, 1,2-dichloro ethane, methyl isobutyl ketone, tetralin and toluene.

U.S. Pat. No. 4,954,260 (Z. Ludmer et al.) discloses a phase-transition type of forward extraction process, but one that uses a change in temperature to induce the phase transition, rather than a change in solvent composition. It describes a multi-stage counter-current process in which phase transition from a single-liquid phase to two liquid phases occurs in each step. The required phase transition is induced through the use of internal heating and cooling coils or other heat transfer means in each stage. The process requires changing temperature in each stage in order to cross a liquid-liquid phase boundary in each stage.

U.S. Pat. No. 6,229,046 B1 (A. Eyal et al.) and U.S. Pat. No. 6,320,077 B1 (A. Eyal et al.) disclose processes for separating lactic acid from a fermentation broth containing free lactic acid and lactic acid salts. Oxygenated solvents that have a multiple number of functional groups (such as alcohol and ether) are mentioned as useful provided they give favorable partitioning of lactic acid. These solvents, however, are not used as extraction solvent themselves but rather in admixture with a tertiary amine (trialkylamine), which is the extraction solvent.

Known liquid-liquid extraction processes used to recover hydrophilic organic compounds from aqueous feeds tend to be expensive, because of having a large number of steps, unfavorable partitioning (uneconomically low K values), poor selectivity for the desired solute, or poor efficiency for recovery of the solvents used. An improved method for recovery of valuable hydrophilic organic compounds from aqueous streams has now been discovered. This method uses certain glycol ethers having specific partition ratio, value K, in known liquid-liquid extraction equipment.

SUMMARY OF THE INVENTION

In one aspect, the present invention concerns a method of separating a hydrophilic organic compound from aqueous liquor comprising the steps of: (a) intermixing a sufficient quantity of a glycol ether with the aqueous liquor at a first temperature to form a suspension comprising an aqueous raffinate phase and a glycol ether extract phase comprising said glycol ether, water in saturated quantity, and a portion of the hydrophilic organic compound, the glycol ether having the formula

$R'—(OCHR''CHR'')_n—O—R'''$ wherein R' is an alkyl group of 1 to 8, preferably 1 to 4, carbon atoms; R'' is, independently in each occurrence, hydrogen, methyl or ethyl; R''' is hydrogen, an alkyl group having from 1 to 4 carbon atoms, a propionyl or an acetyl group; and n is an integer between 1 and 4; with the proviso that R''' is methyl when R' and R'' are each methyl group, and wherein the glycol ether has an inverse solubility in water and the partition ratio, value K, for the hydrophilic organic solute is greater than 0.1; (b) separating the glycol ether extract phase formed in step (a) from the aqueous raffinate phase; (c) heating the glycol ether extract phase obtained in step (b) to a second temperature which is higher than the first temperature to form a suspension comprising an aqueous extract phase containing a portion of the hydrophilic organic compound and a glycol ether raffinate phase; and (d) separating the glycol ether raffinate phase formed in step (c) from the aqueous extract phase.

In another aspect, the present invention concerns the above described method wherein step (d) is replaced with the following two steps: (e) intermixing sufficient quantity of water with the mixture formed in step (c) to form a mixture of a glycol ether raffinate phase further depleted in the hydrophilic organic compound and an aqueous extract phase containing the added water and additional hydrophilic organic compound; and (f) separating the aqueous extract phase formed in step (e) from the glycol ether raffinate phase.

In another aspect the present invention concerns the above described methods wherein the step (c) is conducted in the presence of a hydrophobic organic solvent selected from the group consisting of an alcohol having from 4 to 14 carbon atoms, a ketone having from 4 to 14 carbon atoms, a chlorinated hydrocarbon having from 2 to 6 carbon atoms, an aromatic compound having from 6 to 12 carbon atoms, an ether having from 6 to 19 carbon atoms, and blends thereof.

In another aspect the present invention concerns a method of separating a hydrophilic organic compound from an aqueous liquor comprising the steps of: (a) intermixing a sufficient quantity of a glycol ether with the aqueous liquor at a temperature not more than 30 centigrade degrees above the lower critical solution temperature (LCST) to form a suspension comprising an aqueous raffinate phase and a glycol ether extract phase comprising said glycol ether, water in saturated quantity, and a portion of the hydrophilic organic compound, the glycol ether having the formula

wherein R' is an alkyl group of 1 to 8, preferably 1 to 4, carbon atoms; R" is, independently in each occurrence, hydrogen, methyl or ethyl; R'" is hydrogen, an alkyl group having from 1 to 4 carbon atoms, a propionyl or an acetyl group; an n is an integer between 1 and 4; with the proviso that R'" is methyl when R' and R" are each methyl, and wherein said hydrophilic organic compound is selected from the group consisting of citric acid, lactic acid, formic acid, acetic acid, succinic acid, ascorbic acid, 1,3-propanediol, 1,2-propanediol, glucose, glycerin, and p-toluene sulfonic acid; and (b) separating the glycol ether extract phase formed in step (a) from the aqueous raffinate phase.

DETAILED DESCRIPTION

Figure 1:
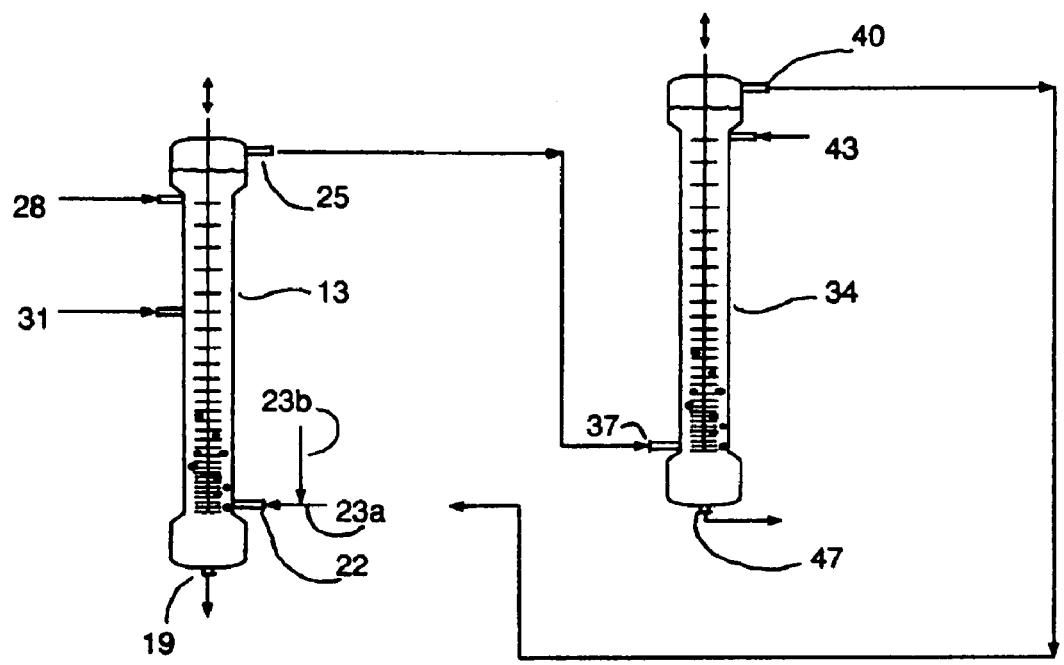
FIG. 1 is a flow diagram for a particular embodiment of the present invention, as discussed further hereinbelow.

The method of the present invention is useful for recovery of valuable hydrophilic organic compounds produced via fermentation or otherwise produced or utilized within a manufacturing process in which said hydrophilic organic compounds must be recovered from a dilute aqueous solution at some point in the fermentation or manufacturing process. The method of the present invention is particularly useful for recovery of hydrophilic organic compounds that are difficult or impossible to recover directly via distillation because of their low volatility with respect to water or because of their thermal instability at distillation temperatures. The hydrophilic organic compounds that can be suitably recovered by the method of the present invention are compounds selected from the group consisting of carboxylic acids, sulfonic acids, polyhydroxy compounds, amino acids, and amides. Preferably, the hydrophilic organic compounds are selected from the group consisting of formic acid, acetic acid, propionic acid, butyric acid, lactic acid, citric acid, benzoic acid, ascorbic acid, adipic acid, succinic acid, methacrylic acid, lauric acid, stearic acid, glycolic acid, glucaric acid, glutamic acid, itaconic acid, levulinic acid, fumaric acid, malic acid, aspartic acid, 3-hydroxypropionic acid, 2,5-furandicarboxylic acid, glycerin, glucose, caprolactam, 3-hydroxybutyrolactone, 1,3-propanediol, 1,2-propanediol, 2,3-butanediol, 1,2,4-butanetriol, xylitol, sorbitol, arabinitol, p-toluene sulfonic acid, methane sulfonic acid, and dodecylbenzene sulfonic acid. More preferably, the hydrophilic organic compounds are selected from the group consisting of formic acid, acetic acid, lactic acid, citric acid, benzoic acid, ascorbic acid, succinic acid, adipic acid, p-toluene sulfonic acid, methane sulfonic acid, dodecylbenzene sulfonic acid, glycerin, glucose, caprolactam, 1,3-propanediol, 1,2-propanediol, 2,3-butanediol and xylitol.

The hydrophilic organic compounds that are recoverable by the method of the present invention must exhibit a partition ratio, value K, greater than 0.10, preferably greater than 0.5, more preferably greater than 1.0, most preferably greater than 1.5. The partition ratio, value K, is defined in terms of Bancroft coordinates; that is, in terms of mass ratios (K=mass of hydrophilic organic compound per mass of glycol ether in the organic phase divided by the mass of hydrophilic organic compound per mass of water in the aqueous phase). The use of Bancroft coordinates is described in Perry's Chemical Engineers' Handbook (Robbins, L. A. and Cusack, R. W., "Liquid-Liquid Extraction Operations and Equipment," Section 15 in Perry's Chemical Engineers' Handbook, 7th ed., R. H. Perry and D. W. Green, editors, McGraw-Hill, New York, 1997). Expressing the partition ratio in terms of mass ratios is desirable because doing so simplifies the material balance and mass-transfer calculations used to analyze process performance, as equilibrium and operating lines tend to be linear over a wide concentration range. The partition ratio for a hydrophilic organic compound varies for each individual glycol ether and can be easily determined by a person of an ordinary skill in the art without undue experimentation.

Suitable glycol ethers for extracting hydrophilic organic compounds in the method of the present invention are selected from the group consisting of dipropylene glycol ethyl ether, tripropylene glycol ethyl ether, propylene glycol isopropyl ether, dipropylene glycol isopropyl ether, tripropylene glycol isopropyl ether, propylene glycol n-propyl ether, dipropylene glycol n-propyl ether, tripropylene glycol n-propyl ether, propylene glycol t-butyl ether, dipropylene glycol t-butyl ether, tripropylene glycol t-butyl ether, propylene glycol n-butyl ether, dipropylene glycol n-butyl ether, tripropylene glycol n-butyl ether, propylene glycol n-pentyl ether, propylene glycol n-hexyl ether, butylene glycol methyl ether, dibutylene glycol methyl ether, ethylene glycol n-butyl ether, ethylene glycol n-pentyl ether, ethylene glycol n-hexyl ether, ethylene glycol n-heptyl ether, ethylene glycol 2-ethylhexyl ether, diethylene glycol n-hexyl ether, propylene glycol methyl ether acetate, propylene glycol ethyl ether acetate, propylene glycol isopropyl ether acetate, propylene glycol n-propyl ether acetate, propylene glycol n-butyl ether acetate, dipropylene glycol methyl ether acetate, dipropylene glycol ethyl ether acetate, ethylene glycol n-butyl ether acetate, propylene glycol isobutyl ether, dipropylene glycol isobutyl ether, tripropylene glycol isobutyl ether, ethylene glycol t-butyl ether, ethylene glycol isobutyl ether, ethylene glycol ethyl ether acetate, ethylene glycol isobutyl ether acetate, diethylene glycol ethyl ether acetate, dipropylene glycol dimethyl ether, and diethylene glycol n-butyl ether acetate and blends thereof. These glycol ethers are well known in the art and various methods for their preparation are described in the literature and practiced commercially.

These glycol ethers exhibit inverse solubility in water such that the solubility in water at 100° C. is at least 1 weight percent less than the solubility in water at −5° C. This inverse solubility behavior can be attributed to temperature-sensitive hydrogen bonding. It is known that many glycol ethers exhibit a lower critical solution temperature (LCST) below which they are completely miscible with water. At temperatures below the LCST, the glycol ether is able to form hydrogen bonds with water and this attractive interaction leads to complete miscibility. At temperatures above the LCST, hydrogen bonding is disrupted by increasing thermal energy and hydrophobic interactions between the glycol ether and water begin to dominate. This results in partial miscibility and a decrease in the solubility of the glycol ether in water with increasing temperature (termed inverse solubility). Depending on the particular glycol ether, the LCST can be as low as −10° C. or as high as 100° C.

The method of the present invention involves the following general steps: (a) intermixing an aqueous stream containing a hydrophilic organic compound with a sufficient amount of a glycol ether at a first temperature to form a suspension comprising an aqueous raffinate phase and a glycol ether extract phase comprising said glycol ether, water in saturated quantity, and a portion of the hydrophilic organic compound (forward extraction); (b) separating the glycol ether extract phase formed in step (a) from the aqueous raffinate phase; (c) heating the glycol ether extract phase obtained in step (b) to a second temperature which is higher than the first temperature to form a suspension comprising an aqueous extract phase containing a portion of the hydrophilic organic compound and a glycol ether raffinate phase (back extraction), and (d) separating the glycol ether raffinate phase formed in step (c) from the aqueous extract phase containing the hydrophilic organic compound. Furthermore, additional steps may be used to enhance the recovery of hydrophilic organic compound. In some embodiments step (d) may be omitted and replaced with the following generalized steps: (e) intermixing a sufficient quantity of water with the mixture formed in step (c) to form a mixture of a glycol ether raffinate phase further depleted in the hydrophilic organic compound and an aqueous extract phase containing the added water and additional hydrophilic organic compound; and (f) separating the aqueous extract phase formed in step (e) from the glycol ether raffinate phase.

In this description of the invention, the term raffinate phase refers to a liquid phase that becomes depleted in hydrophilic organic compound due to transfer of a portion of the hydrophilic organic compound contained in that phase into another liquid phase. The other liquid phase is termed the extract phase. In the forward extraction process (step (a)), the aqueous phase is the raffinate phase and the glycol ether phase is the extract phase. In the back extraction process (step (c)), the glycol ether phase is the raffinate phase and the aqueous phase is the extract phase.

Thus, according to the present invention, a hydrophilic organic compound is extracted from an aqueous stream containing same by a liquid-liquid extraction process involving a forward extraction into a glycol ether extract phase conducted at a first temperature where the K value is effective for transfer of the desired solute into the glycol ether extract phase. This is followed by back extraction of the hydrophilic organic compound from the glycol ether extract phase into water conducted at a second temperature where the K value is lower, favoring partition of the hydrophilic organic compound into water. In certain cases, however, the K value can be the same for both forward and back extraction. The extraction method conditions are determined by the magnitude of the K value for the forward extraction and its temperature sensitivity.

If desired, the glycol ether used in the method of the present invention can be recovered and recycled into the process. The recovery and recycling of the glycol ether must be achieved with little loss of the glycol ether in order to achieve good process economics. Both aqueous raffinate phase and aqueous extract phase containing hydrophilic organic compound become saturated with the glycol ether during the extraction process. Typically, the amount of glycol ether dissolved in these aqueous phases is in the range of from 0.5 to 20 percent by weight. The saturation amount of the glycol ether varies with the particular glycol ether used, the temperature and the presence of other organic components in the solution. It may be desirable to reduce the concentration of the glycol ether left in the aqueous raffinate and aqueous extract phases to levels below the saturation concentration in order to minimize waste treatment requirements, to meet hydrophilic organic compound specifications, and to reduce the need for using additional amounts of glycol ether as make-up solvent. The recovery of glycol ether can be done by any known solvent recovery methods, such as steam stripping, addition of a hydrophobic co-solvent with the glycol ether to reduce the solubility of the glycol ether in the aqueous phase, and extraction of the glycol ether out of the aqueous phase into a hydrophobic organic solvent that is more readily recovered from the aqueous phase.

In cases where the glycol ether used has high relative volatility, the glycol ether can conveniently be recovered for recycle back into the process using steam stripping as the recovery method.

In cases where the glycol ether is not sufficiently hydrophobic and volatile, the steam stripping solvent recovery method is not suitable. In such a case, the addition of a steam-strippable hydrophobic solvent to the aqueous phase containing residual glycol ether provides an efficient method for recovering the glycol ether for recycle back to the method. The hydrophobic solvent extracts the residual glycol ether from the aqueous phase into a second hydrophobic solvent phase. The hydrophobic solvent must have a reasonably high K value for the glycol ether recovery and must be sufficiently hydrophobic and volatile to allow its subsequent removal from water via steam stripping.

The hydrophobic organic solvents that are useful for recovery of glycol ethers in the method of the present invention are selected from the group consisting of an alcohol having from 4 to 14 carbon atoms, a ketone having from 4 to 14 carbon atoms, a halogenated hydrocarbon having from 2 to 6 carbon atoms, an aromatic compound having from 6 to 12 carbon atoms, and an ether having from 6 to 19 carbon atoms. Non-limiting illustrative examples of the hydrophobic organic solvent useful in the method of the present invention are 1-octanol, 2-ethylhexanol, 2-pentanone, 2-nonanone, diisobutylketone, methylisobutylketone, methylene chloride, toluene, dichlorobenzene, and di-n-butyl ether and blends thereof.

The intermixing of the glycol ether with the aqueous stream in step (a) of the method of the present invention is conveniently carried out at a temperature between about −5° C. and 80° C. The temperature should not be more than 30° C., preferably no more than 20° C., more preferably no more than 15° C., above the lower critical solution temperature (LCST). The temperature used is dependent upon the particular glycol ether used. The temperature at which the heating of the liquid organic phase in step (c) of the method of the present invention is carried out is higher than the temperature used in step (a). In general, this temperature shall be between 10° C. and 120° C. and will also depend on the particular glycol ether used.

The method of the present invention is advantageously carried out at atmospheric pressure, although higher and lower pressures may be used in certain cases.

A person of an ordinary skill in the art may readily select the amount of glycol ether and organic hydrophobic solvent that may be used. The glycol ether must be used in sufficient amount to extract a desired portion of the organic hydrophilic compound from the aqueous feed stream. This can be readily determined by experimentation. The required amount of glycol ether may be reduced by using known multi-stage countercurrent liquid-liquid extraction methods.

In general, the hydrophobic organic solvent should be used in sufficient amount to extract a desired portion of the dissolved glycol ether from the aqueous feed solution. This also can be readily determined by experimentation, and the required amount of hydrophobic organic solvent may be reduced by using known multi-stage countercurrent liquid-liquid extraction methods.

The method of the present invention can be carried out in a batch operation or continuously, and may be conducted in any conventional single stage or multiple stage liquid-liquid extraction equipment, including, for example, a countercurrent liquid-liquid extraction column.

The types of extraction equipment useful in the present invention are well known in the art and include, for example, a Karr column extractor and the like. The extraction process can additionally involve various types of known distillation and evaporation equipment for recovery of low-boiling or high-boiling glycol ethers, for isolation of purified hydrophilic organic compound, or for recovery of a hydrophobic organic solvent, if used.

An embodiment of the present invention is illustrated in FIG. 1 wherein two Karr column extractors are used, one for the forward extraction step and the other for the back extraction step. This example is presented here to illustrate and clarify the invention and does not limit the application of the invention in any way.

In the forward extraction step, as illustrated in FIG. 1, an aqueous liquor containing the hydrophilic organic compound of interest is fed into the forward extraction Karr column extractor 13 via aqueous liquor inlet 31 located at the upper section of the column extractor 13. The aqueous liquor forms an aqueous raffinate phase that moves down the column extractor and exits at the bottom via column exit 19. Glycol ether is fed into the forward extraction Karr column extractor 13 via recycle/make-up glycol ether inlet 22 located at the lower section of column extractor 13, forming a glycol ether extract phase that moves up the column extractor 13 and exits at the glycol ether extract phase exit 25, countercurrent to the movement of aqueous raffinate phase. A small amount of wash water may be fed into the forward extraction Karr column extractor 13 via a first water inlet 28 located at the upper section of the column above the aqueous liquor inlet 31, to wash out any impurities such as sugars and the like, from the glycol ether extract phase exiting the column. The wash water becomes part of the aqueous raffinate phase. As the aqueous raffinate phase moves through the forward extraction Karr column extractor 13, a portion of the hydrophilic organic compound transfers into the glycol ether extract phase. The aqueous raffinate phase exiting at the bottom of the column extractor 13 contains glycol ether in saturated quantity. The glycol ether extract phase exiting the column at glycol ether extract phase exit 25 contains water in saturated quantity and a portion of the hydrophilic organic compound that enters the Karr column extractor 13 in the aqueous liquor. This forward extraction Karr column extractor 13 is held at a low temperature at which the value K for the hydrophilic organic compound is high such that the amount of glycol ether needed to cause transfer of a desired portion of the hydrophilic organic compound out of the aqueous liquor into the glycol ether extract phase is reduced. The organic extract phase that exits the forward extraction Karr column extractor 13 at glycol ether extract phase exit 25 is fed into the second, back extraction Karr column extractor 34 for the back extraction.

The same process may be conducted using other types of extraction equipment, including a mixer-settler cascade involving separate multiple liquid-liquid mixing stages and liquid-liquid separation stages. In general, the upper section of the forward extraction Karr column extractor 13 shown in FIG. 1 depicts the feed end of the forward extraction process, and the lower section of the forward extraction Karr column extractor 13 shown in FIG. 1 depicts the raffinate end of the forward extraction process. FIG. 1 also illustrates the case in which the glycol ether extract phase has a specific gravity lower than that of the aqueous raffinate phase. This is normally the case, but in a few cases the specific gravity of the glycol ether extract phase may be greater than that of the aqueous raffinate phase. A person knowledgeable in the art of extraction will recognize how the invention illustrated in FIG. 1 can be implemented using other types of extraction equipment and different relative specific gravities.

In the back extraction step, as illustrated in FIG. 1, the glycol ether extract phase exiting the forward extraction Karr column extractor 13 from glycol ether extract phase exit 25 is fed into the back extraction Karr column extractor 34 via glycol ether extract phase inlet 37 located at the bottom section of the column extractor 34. The glycol ether contained in this stream forms a glycol ether raffinate phase within the back extraction Karr column extractor 34 that moves up the column and exits at the top from glycol ether raffinate phase exit 40. Clean water is fed into the back extraction Karr column extractor 34 via a second water inlet 43 located at the upper section of the column extractor 34. The clean water forms an aqueous extract phase that moves down the column countercurrent to the movement of glycol ether raffinate phase and exits at the bottom from aqueous extract phase exit 47. As the glycol ether raffinate phase moves through the column, a portion of the hydrophilic organic compound transfers into the aqueous extract phase. The glycol ether raffinate phase exiting the column from glycol ether raffinate phase exit 40 at the top contains water in saturated quantity. The aqueous extract phase exiting the column at the bottom via aqueous extract phase exit 47 contains glycol ether in saturated quantity and a portion of the hydrophilic organic compound that enters the back extraction Karr column extractor 34 in the glycol ether extract phase produced in the forward extraction Karr column extractor 13. The back extraction Karr column extractor 34 is held at a higher temperature than the forward extraction Karr column extractor 13. At this higher temperature, the value K for the hydrophilic organic compound is generally lower than at forward-extraction conditions, and the amount of clean water needed to cause transfer of a desired portion of the hydrophilic organic compound into the aqueous extract phase is reduced. The partition ratio, value K, can be the same or different in the forward and back extraction steps; however, it is preferred that the value of K is lower in the back extraction step compared to the forward extraction step, since this allows a reduction in the amount of clean water and an increase in the concentration of hydrophilic organic compound in the aqueous extract phase. Glycol ether is recovered from the organic raffinate phase (exiting via glycol ether raffinate phase exit 40) and is recycled back into the forward extraction Karr column extractor 13 (via recycle/make-up glycol ether inlet 22, that is, glycol ether from both recycle and make-up sources is hereby introduced, as suggested by arrows 23a, for recycle glycol ether, and 23b, for make-up glycol ether).

The same process may be conducted using other types of extraction equipment, including a mixer-settler cascade involving separate multiple liquid-liquid mixing stages and liquid-liquid separation stages. In general, the lower section of the back extraction Karr column extractor 34 shown in FIG. 1 depicts the feed end of the back extraction process, and the upper section of the back extraction Karr column extractor 34 shown in FIG. 1 depicts the raffinate end of the back extraction process. FIG. 1 also illustrates the case in which the glycol ether raffinate phase has a specific gravity lower than that of the aqueous extract phase. This is normally the case, but in a few cases the specific gravity of the glycol ether raffinate phase may be greater than that of the aqueous extract phase. A person knowledgeable in the art of extraction will recognize how the invention illustrated in FIG. 1 can be implemented using other types of extraction equipment and different relative specific gravities.

If desired, additional equipment can be used in the method of the present invention such as additional extraction, distillation or evaporation equipment for purging impurities from the glycol ether raffinate phase prior to recycle back into the forward extraction step, for isolating hydrophilic organic compound from the aqueous extract phase, for recovery of dissolved glycol ether from the aqueous raffinate phase and the aqueous extract phase, and for recovery and recycle of the hydrophobic solvent, when used. Such additional equipment and its use in liquid-liquid extraction methods are well known in the art. A person of an ordinary skill in the art would use such additional equipment or combination thereof in the method of the present invention in a manner known for use of such equipment in conventional liquid-liquid extraction methods. The use of such additional equipment or combination thereof will depend on many factors, such as, for example, the nature of the hydrophilic organic compound, the nature of other compounds present in the aqueous feed, the nature of the glycol ether used, the use of the hydrophobic organic solvent, the costs associated with the use of glycol ether and/or hydrophobic solvent, the costs associated with the use of additional equipment, and the overall economics of the entire process.

In some cases the glycol ether extract phase comprising glycol ether and hydrophilic organic compound may be fed directly into distillation or evaporation equipment wherein the glycol ether is separated from the hydrophilic organic compound, avoiding the back extraction step. This is not always practical; however, due to instability of the hydrophilic organic compound at the distillation conditions or because of high costs associated with the required equipment which may include expensive items such as high-vacuum equipment and wiped-film evaporators. When feasible, the glycol ether separated this way is recycled back into the forward extraction step.

The glycol ether dissolved in the aqueous raffinate phase exiting the forward extraction step, and glycol ether dissolved in the aqueous extract phase exiting the back extraction step, may be recovered using known methods, such as, for example by steam stripping or distillation, or by extraction with a hydrophobic organic solvent and combined with the glycol ether recovered from the organic raffinate phase for recycle back into the process. The efficacy of the various recovery methods depends upon the nature of the glycol ether dissolved in the aqueous phase, in particular the relative volatility of the glycol ether with respect to water and the partition ratio for extraction of glycol ether from the aqueous phase into a hydrophobic organic solvent phase. If a hydrophobic organic solvent is used, it should be one for which the saturation amount dissolved in the aqueous phase can be removed via steam stripping.

The purpose of using hydrophobic organic solvent in the invention can be two fold. In one case, the hydrophobic organic solvent can be used to extract dissolved glycol ether from the aqueous raffinate or aqueous extract phases as described above. In another case, it can be used in step (c) to lower the partition ratio, value K, for the hydrophilic compound. In a method of the present invention wherein a hydrophobic organic solvent is used in step (c), the organic raffinate phase comprising the glycol ether and the hydrophobic organic solvent exiting from the top of the back extraction step is fed into distillation equipment wherein the glycol ether is separated from the hydrophobic organic solvent. The separated glycol ether can be recycled back into the process.

All parts, percentages and ratios herein are by weight unless otherwise indicated. The invention will be further clarified by a consideration of the following examples, which are intended to be purely exemplary thereof.

SPECIFIC EMBODIMENTS OF THE INVENTION

Solubility experiments were conducted in a jacketed glass apparatus equipped with a thermowell, a motor-driven glass stirrer with short baffles, a water-cooled condenser, a top sampling port, and a bottom stopcock valve. The temperature in the apparatus was adjusted by circulating a 50/50 propylene glycol/water solution through the jacket with a Brinkmann Lauda RM6 Heating/Cooling Circulator attached to the apparatus with hoses. This set up allowed experiments to be run in the −15° C. to 100° C. temperature range, although most were conducted in the 0° C. to 95° C. range.

Examples 1-18

Example 1

Into the apparatus, through the sample port, were placed approximately 50.0 g dipropylene glycol n-butyl ether (DPnB) and approximately 50.0 g of a 10 percent aqueous lactic acid solution. The sample port was covered with a glass stopper. The water to the condenser was turned on, and the stirrer started and set to agitate the mixture at 800 rpm. The circulator was turned on and set for 0° C. The mixture was stirred continuously as it reached the set point and for ten minutes after the set point was reached. The stirrer was then turned off and the mixture was allowed to separate into two clear layers before collecting samples. Once the samples had been collected, the circulator was reset for 95° C. where a new set of samples was taken.

At each temperature, four samples were taken (two from the top layer and two from the bottom layer). Samples of the bottom layer were collected through the bottom stopcock. Samples of the top layer were taken through the sample port in the lid using a disposable syringe with a long needle. Samples for the gas chromatography (GC) analyses were placed in tared 4-dram vials and weighed. Samples for titration were placed in 100-mL disposable titration cups and weighed. Approximately, 0.5 g was collected for the GC analyses, and approximately 1.0 g for the titration analyses.

Acid concentrations were determined by autotitration with 0.5 M KOH. Water and glycol ether concentrations were determined by GC with a Zebron ZB-1 column. The samples were diluted 5× with THF, the internal standard. The partition ratios, value K, for the forward extraction and the back extraction of lactic acid were calculated from the data generated from the samples and were found to be 1.2 and 0.47, respectively (see Table 1).

Example 2

Partition ratios were obtained for a 10 percent aqueous citric acid solution with ethylene glycol n-hexyl ether (Ehex) using the procedure described in Example 1. The partition ratios are shown in Table 1.

Example 3

Partition ratios were obtained for a 10 percent aqueous citric acid solution with propylene glycol n-propyl ether (PnP) using the procedure described in Example 1. The partition ratios are shown in Table 1.

Example 4

Partition ratios were obtained for a 10 percent aqueous acetic acid solution with DPnB using the procedure described in example 1. The partition ratios are shown in Table 1.

Example 5

Partition ratios were obtained for a 10 percent aqueous glycerin solution with DPnB using the procedure described in Example 1. The partition ratios are shown in Table 1.

Example 6

Partition ratios were obtained for a 2 percent aqueous adipic acid solution with PnP using the procedure described in Example 1. The partition ratios are shown in Table 1.

Example 7

Partition ratios were obtained for a 5 percent aqueous succinic acid solution with PnP using the procedure described in Example 1. The partition ratios are shown in Table 1.

Example 8

Partition ratios were obtained for a 10 percent aqueous ascorbic acid solution with PnP using the procedure described in Example 1. The partition ratios are shown in Table 1.

Example 9

Partition ratios were obtained for a 10 percent aqueous 1,3-propanediol solution with PnP using the procedure described in Example 1. The partition ratios are shown in Table 1.

Example 10

Partition ratios were obtained for a 10 percent aqueous glucose solution with PnP using the procedure described in Example 1. The partition ratios are shown in Table 1.

Example 11

Partition ratios were obtained for a 10 percent aqueous citric acid solution (with 1 percent glucose present) with PnP using the procedure described in Example 1. The partition ratios are shown in Table 1.

Example 12

Partition ratios were obtained for a 0.4 percent aqueous L-glutamic acid solution with PnP using the procedure described in Example 1. The partition ratios are shown in Table 1.

Example 13

Partition ratios were obtained for an 8 percent aqueous itaconic acid solution with PnP using the procedure described in Example 1. The partition ratios are shown in Table 1.

Example 14

Partition ratios were obtained for a 10 percent aqueous levulinic acid solution with PnP using the procedure described in Example 1. The partition ratios are shown in Table 1.

Example 15

Partition ratios were obtained for a 10 percent aqueous levulinic acid solution with PnB using the procedure described in Example 1. The partition ratios are shown in Table 1.

Example 16

Partition ratios were obtained for a 9 percent aqueous malic acid solution with PnP using the procedure described in Example 1. The partition ratios are shown in Table 1.

Example 17

Partition ratios were obtained for a 10 percent aqueous 1,2,4-butanetriol solution with PnP using the procedure described in Example 1. The partition ratios are shown in Table 1.

Example 18

Partition ratios were obtained for a 10 percent aqueous D-sorbitol with PnP using the procedure described in Example 1. The partition ratios are shown in Table 1.

TABLE 1

Forward and Back Extraction Partition Ratios.

| | | | Forward extraction | | Back Extraction | |
|---|---|---|---|---|---|---|
| Example | Glycol Ether | Hydrophilic Organic Compound | Temperature (° C.) | Partition Ratio (K) | Temperature (° C.) | Partition Ratio (K) |
| 1 | DPnB | Lactic Acid* | 0 | 1.2 | 95 | 0.47 |
| 2 | Ehex | Citric Acid* | 5 | 0.82 | 80 | 0.23 |
| 3 | PnP | Citric Acid* | 45 | 1.3 | 95 | 0.44 |
| 4 | DPnB | Acetic Acid* | 0 | 1.79 | 80 | 0.76 |
| 5 | DPnB | Glycerin* | 0 | 1.1 | 80 | 1.1 |
| 6 | PnP | Adipic Acid** | 40 | 2.9 | 80 | 2.8 |
| 7 | PnP | Succinic Acid*** | 40 | 1.5 | 80 | 1.2 |
| 8 | PnP | Ascorbic Acid* | 50 | 0.5 | 80 | 0.3 |
| 9 | PnP | 1,3-Propanediol* | 55 | 1.0 | 80 | 0.7 |
| 10 | PnP | Glucose* | 20 | 0.14 | 80 | 0.04 |
| 11 | PnP | Citric Acid# | 45 | 1.0 | 80 | 0.5 |
| 12 | PnP | L-Glutamic Acid### | 40 | 0.2 | 85 | 0.5 |
| 13 | PnP | Itaconic Acid## | 45 | 2.2 | 80 | 2.0 |
| 14 | PnP | Levulinic Acid* | 50 | 1.6 | 85 | 1.1 |
| 15 | PnB | Levulinic Acid* | 0 | 1.4 | 80 | 1.2 |
| 16 | PnP | Malic Acid# | 45 | 1.0 | 85 | 0.5 |
| 17 | PnP | 1,2,4-Butanetriol* | 40 | 1.1 | 85 | 0.7 |
| 18 | PnP | D-Sorbitol* | 40 | 0.18 | 85 | 0.16 |

*10% aqueous solution
**2% aqueous solution
***5% aqueous solution
0.4% aqueous solution
8–9% aqueous solution
10% aqueous solution in the presence of 1% glucose Examples 19-31

Partition ratios for extraction of PnP from aqueous solution using various hydrophobic organic solvents were obtained in examples 19-31. These are examples for the recovery of a glycol ether from an aqueous phase using a hydrophobic organic solvent.

Example 19

Into the apparatus, through the sample port, were placed approximately 40.0 g 2-ethylhexanol and approximately 40.0 g of a 10 percent aqueous PnP solution. The sample port was covered with a glass stopper. The water to the condenser was turned on, and the stirrer started and set to agitate the mixture at 800 rpm. The circulator was turned on and set for 40° C. The mixture was stirred continuously as it reached the set point and for ten minutes after the set point was reached. The stirrer was then turned off and the mixture was allowed to separate into two clear layers before collecting samples. Once the samples had been collected, the circulator was reset for 60° C., 80° C., and 95° C. where a new set of samples was taken at each temperature.

At each temperature, two samples were taken (one from the top layer and one from the bottom layer). Samples of the bottom layer were collected through the bottom stopcock. Samples of the top layer were taken through the sample port in the lid using a disposable syringe with a long needle. Samples were taken for gas chromatograph (GC) analyses and were placed in tared 4-dram vials and weighed. Approximately 0.5 g was collected for the GC analyses.

Water, glycol ether, and hydrophobic organic solvent concentrations were determined by GC with a Zebron ZB-1 column. The samples were diluted 5 times with tetrahydrofuran (THF), the internal standard. The partition ratios, value K, at each temperature were calculated from the data generated from the samples and were found to be K=12.7 at 40° C., K=23.0 at 60° C., K=35.7 at 80° C., and K=42.7 at 95° C. The partition ratio at 95° C. is shown in Table 2.

Example 20

Partition ratios were obtained for a 10 percent aqueous PnP solution with 1-octanol using the procedure described in Example 19. The maximum partition ratio obtained is shown in Table 2.

Example 21

Partition ratios were obtained for a 10 percent aqueous PnP solution with 2-pentanone using the procedure described in Example 19. The maximum partition ratio obtained is shown in Table 2.

Example 22

Partition ratios were obtained for a 10 percent aqueous PnP solution with methyl isobutyl ketone (MIBK) using the procedure described in Example 19. The maximum partition ratio obtained is shown in Table 2.

Example 23

Partition ratios were obtained for a 10 percent aqueous PnP solution with 2-nonanone using the procedure described in Example 19. The maximum partition ratio obtained is shown in Table 2.

Example 24

Partition ratios were obtained for a 10 percent aqueous PnP solution with di-isobutyl ketone (DIBK) using the procedure described in Example 19. The maximum partition ratio obtained is shown in Table 2.

Example 25

Partition ratios were obtained for a 10 percent aqueous PnP solution with methylene chloride using the procedure described in Example 19. The maximum partition ratio obtained is shown in Table 2.

Example 26

Partition ratios were obtained for a 10 percent aqueous PnP solution with tert-butyl methyl ether (MTBE) using the procedure described in Example 19. The maximum partition ratio obtained is shown in Table 2.

Example 27

Partition ratios were obtained for a 10 percent aqueous PnP solution with toluene using the procedure described in Example 19. The maximum partition ratio obtained is shown in Table 2.

Example 28

Partition ratios were obtained for a 10 percent aqueous PnP solution with dichlorobenzene using the procedure described in Example 19. The maximum partition ratio obtained is shown in Table 2.

Example 29

Partition ratios were obtained for a 10 percent aqueous PnP solution with n-butyl ether using the procedure described in Example 19. The maximum partition ratio obtained is shown in Table 2.

Example 30

Partition ratios were obtained for a 10 percent aqueous PnP solution with cyclohexane using the procedure described in Example 19. The maximum partition ratio obtained is shown in Table 2.

Example 31

Partition ratios were obtained for a 10 percent aqueous PnP solution with kerosene using the procedure described in Example 19. The maximum partition ratio obtained is shown in Table 2.

TABLE 2

Maximum Partition Ratio for Transfer of PnP from a 10% Aqueous PnP Solution into Various Hydrophobia Organic Solvents.

| Example | Hydrophilic Organic Solvent | Temperature (° C.) | Partition Ratio (K) |
|---------|-----------------------------|--------------------|---------------------|
| 19 | 2-Ethylhexanol | 95 | 42.7 |
| 20 | 1-Octanol | 95 | 22.9 |
| 21 | 2-Pentanone | 85 | 21.1 |
| 22 | MIBK | 95 | 17.3 |
| 23 | 2-Nonanone | 95 | 12.8 |
| 24 | DIBK | 95 | 12.2 |
| 25 | Methylene Chloride | 35 | 11.1 |
| 26 | MTBE | 45 | 10.2 |
| 27 | Toluene | 95 | 9.8 |
| 28 | Dichlorobenzene | 95 | 7.2 |
| 29 | n-Butyl Ether | 95 | 6.7 |
| 30 | Cyclohexane | 67 | 4.0 |
| 31 | Kerosene | 95 | 3.3 |

Example 32

This is an example for the recovery of a glycol ether from water in the presence of the hydrophilic organic compound. Partition ratios were obtained for PnP and citric acid in the presence of same using 2-ethylhexanol and the procedure described in example 19. The aqueous charge consisted of 10 percent PnP and 10 percent citric acid. At 95° C., PnP had a partition ratio K=19.4 and citric acid had a partition ratio K=0.03. These results show that the glycol ether can be recovered effectively by the hydrophobic organic solvent without much loss of the hydrophilic organic compound.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

The invention claimed is:

1. A method of separating a hydrophilic organic compound from an aqueous liquor comprising the steps of:
   (a) intermixing a sufficient quantity of a glycol ether with the aqueous liquor at a first temperature, which is no more than 20 centigrade degrees above the lower critical solution temperature, to form a suspension comprising an aqueous raffinate phase and a glycol ether extract phase comprising said glycol ether, water in saturated quantity, and a portion of the hydrophilic organic compound, the glycol ether having the formula $R'-(OCHR''CHR'')_n-O-R'''$ wherein R' is an alkyl group of 1 to 8 carbon atoms; R'' is in one occurrence hydrogen, and in the other occurrence methyl or ethyl; R''' is hydrogen; and n is an integer between 1 and 4; and wherein the glycol ether has an inverse solubility in water and the partition ratio, value K, for the hydrophilic organic compound is greater than 1.0;
   (b) separating the glycol ether extract phase formed in step (a) from the aqueous raffinate phase;
   (c) heating the glycol ether extract phase obtained in step (b) to a second temperature which is higher than the first temperature to form a suspension comprising an aqueous extract phase containing a portion of the hydrophilic organic compound and a glycol ether raffinate phase; and
   (d) separating the glycol ether raffinate phase formed in step (c) from the aqueous extract phase.

2. The method of claim 1, wherein the step (c) is conducted in the presence of a hydrophobic organic solvent selected from the group consisting of an alcohol having from 4 to 14 carbon atoms, a ketone having from 4 to 14 carbon atoms, a chlorinated hydrocarbon having from 2 to 6 carbon atoms, an aromatic compound having from 6 to 12 carbon atoms, and an ether having from 6 to 19 carbon atoms, and blends thereof.

3. The method of claim 1 wherein step (d) includes the following steps:
   (e) intermixing a sufficient quantity of water with the mixture formed in step (c) to form a mixture of a glycol ether raffinate phase further depleted in the hydrophilic organic compound and an aqueous extract phase containing the added water and additional hydrophilic organic compound; and
   (f) separating the aqueous extract phase formed in step (e) from the glycol ether raffinate phase.

4. The method of claim 1, wherein the steps of intermixing and separating phases are conducted in counter-current multistage extraction equipment.

5. The method of claim 1, wherein the aqueous raffinate phase separated in step (b) or the aqueous extract phase separated in step (d) are further contacted with a hydrophobic organic solvent or blends thereof to recover residual glycol ether.

6. The method of claim 3, wherein the aqueous extract phase separated in step (f) is further contacted with a hydrophobic organic solvent or blends thereof to recover residual glycol ether.

7. The method of claim 1, wherein the hydrophilic organic compound is a compound selected from the group consisting of carboxylic acids, sulfonic acids, polyhydroxy compounds, amino acids and amides.

8. The method of claim 7, wherein the hydrophilic organic compound is selected from the group consisting of formic acid, acetic acid, propionic acid, butyric acid, lactic acid, citric acid, benzoic acid, ascorbic acid, adipic acid, succinic acid, methacrylic acid, lauric acid, stearic acid, glycolic acid, glycerin, glucose, caprolactam, 1,3-propanediol, 1,2-propanediol, 2,3-butanediol, xylitol, p-toluene sulfonic acid, methane sulfonic acid, and dodecylbenzene sulfonic acid.

9. The method of claim 1, wherein the partition ratio, K value, is greater in step (a) than in step (c).

10. The method of claim 2, wherein the hydrophobic organic solvent is selected from the group consisting of 1-octanol, 2-ethylhexanol, 2-pentanone, 2-nonanone, diisobutylketone, methylisobutylketone, methylene chloride, toluene, dichlorobenzene, and di-n-butyl ether and blends thereof.

11. The method of claim 1, wherein the glycol ether is selected from the group consisting of dipropylene glycol ethyl ether, tripropylene glycol ethyl ether, propylene glycol isopropyl ether, dipropylene glycol isopropyl ether, tripropylene glycol isopropyl ether, propylene glycol n-propyl ether, dipropylene glycol n-propyl ether, tripropylene glycol n-propyl ether, propylene glycol t-butyl ether, dipropylene glycol t-butyl ether, tripropylene glycol t-butyl ether, propylene glycol n-butyl ether, dipropylene glycol n-butyl ether, tripropylene glycol n-butyl ether, propylene glycol n-pentyl ether, propylene glycol n-hexyl ether, butylene glycol methyl ether, dibutylene glycol methyl ether, propylene glycol isobutyl ether, dipropylene glycol isobutyl ether, tripropylene glycol isobutyl ether, and blends thereof.

12. A method of separating a hydrophilic organic compound from an aqueous liquor comprising the steps of:
(a) intermixing a sufficient quantity of a glycol ether with the aqueous liquor at a temperature not more than 20 centigrade degrees above the lower critical solution temperature (LCST) to form a suspension comprising an aqueous raffinate phase and a glycol ether extract phase comprising said glycol ether, water in saturated quantity, and a portion of the hydrophilic organic compound, the glycol ether having the formula

wherein R' is an alkyl group of 1 to 8 carbon atoms; R" is in one occurrence hydrogen, and in the other occurrence methyl or ethyl; R''' is hydrogen, and n is an integer between 1 and 4; and wherein said hydrophilic organic compound is selected from the group consisting of citric acid, lactic acid, formic acid, acetic acid, succinic acid, ascorbic acid, 1,3-propanediol, 1,2-propanediol, glycerin, and p-toluene sulfonic acid; and
(b) separating the glycol ether extract phase formed in step (a) from the aqueous raffinate phase.

13. The method of claim 12, wherein the steps of intermixing and separating phases are conducted in counter-current multistage extraction equipment.

* * * * *